United States Patent
Tanaka

[11] Patent Number: 5,827,175
[45] Date of Patent: Oct. 27, 1998

[54] ENDOSCOPICALLY INSERTING ULTRASOUND PROBE

[75] Inventor: Toshizumi Tanaka, Omiya, Japan

[73] Assignee: Fuji Photo Optical Co., Ltd., Omiya, Japan

[21] Appl. No.: 939,697

[22] Filed: Sep. 29, 1997

[30] Foreign Application Priority Data

Sep. 30, 1996 [JP] Japan .................................. 8-276903
Sep. 30, 1996 [JP] Japan .................................. 8-276904

[51] Int. Cl.$^6$ .......................................................... A61B 1/00
[52] U.S. Cl. ............................................ 600/104; 600/459
[58] Field of Search ...................................... 600/104, 109, 600/127, 137, 149, 150, 407, 437, 439, 459

[56] References Cited

U.S. PATENT DOCUMENTS

5,158,086  10/1992  Brown et al. ............................. 600/459
5,417,216   5/1995  Tanaka .
5,596,991   1/1997  Tanaka .
5,690,110  11/1997  Tanaka .

*Primary Examiner*—Beverly M. Flanagan
*Attorney, Agent, or Firm*—Oblon, Spivak, McClelland, Maier & Neustadt, P.C.

[57] ABSTRACT

An endoscopically inserting ultrasound probe to be placed in an instrument channel within an insertion rod of an endoscope at the time of introduction into a body cavity, and having a probe head section housing an ultrasound transducer at the fore end of an elongated flexible cord member with a connector section in a proximal end portion thereof for connection to a probe controller unit. The endoscopically inserting ultrasound probe is provided with a probe head with an outside diameter much larger than the inside diameter of an instrument channel within an endoscopic insertion rod, permitting to use an ultrasound transducer of a large size. The ultrasound probe is adapted to be placed in an endoscopic instrument channel in an inverse fashion, through an exit opening of instrument channel, which is provided at the fore distal end of an endoscopic insertion rod, and from a connector section provided at the proximal end of a flexible cord member.

12 Claims, 12 Drawing Sheets

ENDOSCOPICALLY INSERTING ULTRASOUND PROBE

BACKGROUND OF THE INVENTION

1. Field of the Art

This invention relates to an endoscopically inserting ultrasound probe, and more particularly to an ultrasound probe to be introduced into a body cavity by way of a biopsy or instrument channel of an endoscope for internal ultrasound examinations.

2. Prior Art

Ultrasound probes have been in wide use, for example, for acquiring information on internal tissue conditions of patient. In certain types of ultrasound probe, an ultrasound transducer is mounted on a distal end portion of a catheter-like elongated flexible insertion member and thereby introduced into a body cavity to transmit ultrasound signals toward body tissues of particular interest through an intracavitary wall. The ultrasound probe of this sort has an advantage that ultrasound signals can be transmitted to a target spot from a close distance without influenced by subcutaneous fat. The ultrasound probes are used for the so-called ultrasound endoscopes which are adapted to be directly inserted into a body cavity, as well as for the endoscopically inserting ultrasound probes to be introduced into a body cavity by way of and under the guidance of a biopsy or instrument channel of an endoscope as described, for example, in U.S. Pat. No. 4,802,487 and U.S. Pat. No. 5,211,176. The existing ultrasound examination systems using a probe of this sort are generally constituted by a catheter-like probe member of a shape suitable for placement in an instrument channel of an endoscope, a probe controller unit to be manipulated by an operator for controlling ultrasound scanning operations by the probe member, and an ultrasound image observation terminal including an ultrasound signal processor and a monitor screen for producing ultrasound images on the basis of echo signals received by the probe member. The catheter-like probe member is provided with an ultrasound probe head at the distal end of an elongated flexible cord member, the probe head housing an ultrasound transducer which is connected to the ultrasound image observation terminal through the flexible cord member via the probe controller unit.

On the other hand, the instrument channel on the part of endoscope is extended all the way through an endoscopic insertion rod from an entrance opening, which is provided on a manipulating head of the endoscope, to an exit opening which is provided on a distal end face or on a lateral side of a distal end portion of the endoscopic insertion rod. At the time of an ultrasound examination, the above-described ultrasound probe is inserted into the instrument channel of the endoscope in such a way that the ultrasound probe head at the fore distal end of the cord member is protruded over a predetermined length from the exit opening of the endoscopic instrument channel. In this protruded position, the transducer on the ultrasound probe head is activated to make ultrasound scans. The exit opening of the instrument channel is located in the vicinity of illumination and observation windows of an endoscopic observation systen, so that the ultrasound scans can be made simultaneously and in relation with an endoscopic examination by the endoscopic observation system whenever necessary.

In making ultrasound scans in this manner, the frequency and power of ultrasound pulse signals, which are transmitted by the ultrasound transducer on the probe head, depend on its size. Generally, with an ultrasound transducer of a larger size, namely, with an ultrasound transducer with a larger transmission surface area, it becomes possible to transmit ultrasound signals of lower frequency and greater power. High-output low-frequency ultrasound pulse signals can reach greater depths in the body and send back greater echoes. Besides, an ultrasound transducer with a broader active surface is superior in signal receptivity. Accordingly, the use of a large-size ultrasound transducers will result in improvements in receptivity of return echo signals and S/N ratio, making it possible to produce clearer ultrasound images on the basis of return echo signals and to improve the accuracy of ultrasound examinations. However, the ultrasound transducer on an endoscopically inserting ultrasound probe, which uses an endoscopic instrument channel as a guide for insertion into a body cavity, is naturally limited in size. For these reasons, the endoscopically inserting ultrasound probes have been used only for specific purposes, for example, for making ultrasound scans for any disorder which may exist in tissues immediately under mucosa.

SUMMARY OF THE INVENTION

With the foregoing situations in view, it is a primary object of the present invention to provide an endoscopically inserting ultrasound probe employing an ultrasound transducer of a large size, much larger than the inside diameter of the biopsy or instrument channels on the part of endoscope.

It is another object of the present invention to provide an endoscopically inserting ultrasound probe which is capable of transmitting low-frequency and high-power ultrasound pulse signals from an ultrasound transducer on a probe head.

In accordance with the present invention, the above-stated objectives are achieved by the provision of an endoscopically inserting ultrasound probe which is adapted to be placed in an instrument channel within an insertion rod of an endoscope at the time of insertion into a body cavity and provided with a probe head housing an ultrasound transducer at the fore end of an elongated flexible cord member having a connector section at the proximal end portion thereof for connection to a probe controller unit, the endoscopically inserting ultrasound probe being characterized by: a probe head section having an outside diameter larger than inside diameter of an instrument channel within an endoscopic insertion rod; and an elongated flexible cord member with an outside diameter smaller than the inside diameter of the endoscopic instrument channel, including a connector section at the proximal end of the flexible cord member; the ultrasound probe being adapted to be placed in the endoscopic instrument channel inversely through an exit opening of the instrument channel provided at the fore distal end of the endoscopic insertion rod and from the connector section at the proximal end of the flexible cord member.

In the case of an ultrasound probe having a large probe head as described above, the ultrasound probe has to be placed in an endoscopic instrument channel prior to introduction into a body cavity. The probe head which is connected to the fore end of an elongated flexible cord member of endoscopically inserting ultrasound probe usually has a rigid housing structure for an ultrasound transducer. Therefore, if the probe head, which is projected from the fore distal end of the endoscopic instrument channel, is left in a free state, it tends to swing unstably in arbitrary directions at the distal end of the endoscopic insertion rod in such a way as to hinder the introduction of the endoscope into a body cavity. The instability of the probe head could make it difficult to position the ultrasound transducer correctly relative to intracavitary wall areas to be scanned.

According to the present invention, the problems of this nature are precluded by the use of a probe head holder member which is adapted to receive and hold a neck portion of the ultrasound probe head fixedly in or in front of an exit opening of the instrument channel at the fore distal end of the endoscopic insertion rod.

BRIEF DESCRIPTION OF THE DRAWINGS

The above and other objects, features and advantages of the present invention will become apparent from the following particular description of the invention, taken in conjunction with the accompanying drawings which show by way of example some preferred embodiments of the invention and in which.

DESCRIPTION OF PREFERRED EMBODIMENTS

Hereafter, the invention is described more particularly by way of its preferred embodiments with reference to the accompanying drawings.

Figure 1:
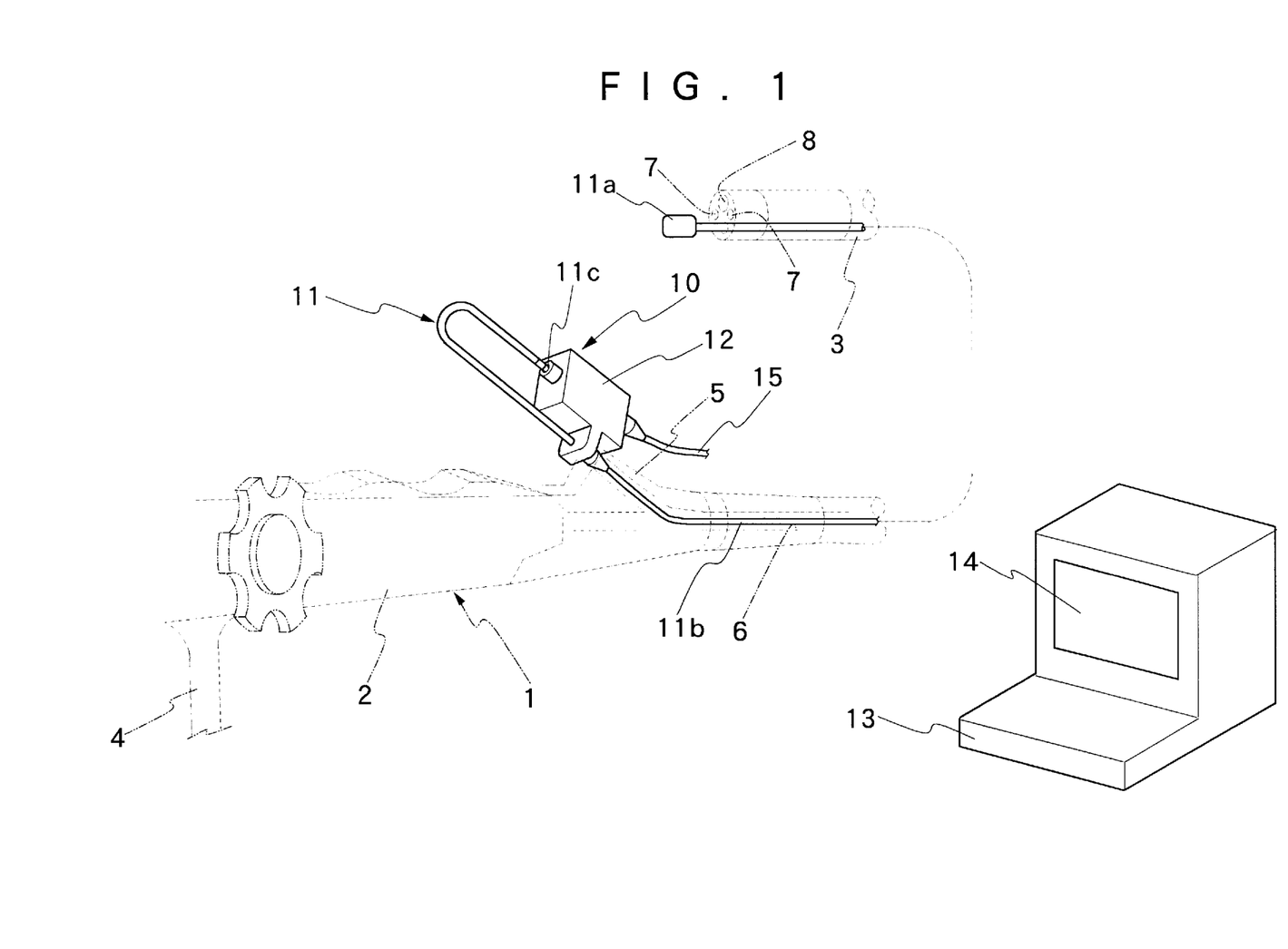
FIG. 1 is a schematic illustration of an ultrasound examination system, employing an endoscopically inserting ultrasound probe according to the present invention, the ultrasound probe being placed in an instrument channel of an endoscope in preparation for introduction into a body cavity.

Referring first to FIG. 1, there is schematically shown the general layout of an ultrasound examination system having an endoscopically inserting ultrasound probe, wherein indicated generally at 1 is an endoscope and at 10 is the ultrasound examination system.

Connected to front and rear ends of a manipulating head grip 2 of the endoscope 1 are an insertion rod 3 to be introduced into a body cavity and a universal cable 4 which connects the endoscope to a light source. Provided on the manipulating head grip 2 is a housing of an approach way 5 to a biopsy channel or instrument channel 6 of the endoscope 1. Namely, the approach way 5 is connected to a proximal end portion of the instrument channel 6 which is extended internally of the endoscope between the manipulating head grip 2 to the fore distal end of the insertion rod 3. The instrument channel 6 is opened to the outside at the fore end of the insertion rod 3 in the vicinity of illumination and observations windows 7 and 8 which constitute part of the endoscopic observation means.

The ultrasound examination system 10 is largely constituted by an ultrasound probe 11, a probe controller unit 12 and an ultrasound image observation terminal 13 with a viewing screen or an ultrasound image monitor 14. The ultrasound probe 11 includes an ultrasound probe head 11a containing an ultrasound scanner and an elongated flexible cord member 11b with a connector section 11c. The connector 11c is disconnectibly plugged in the probe controller unit 12, which is in turn disconnectibly connected to the ultrasound image observation terminal 13 through a cable 15.

Figure 2:
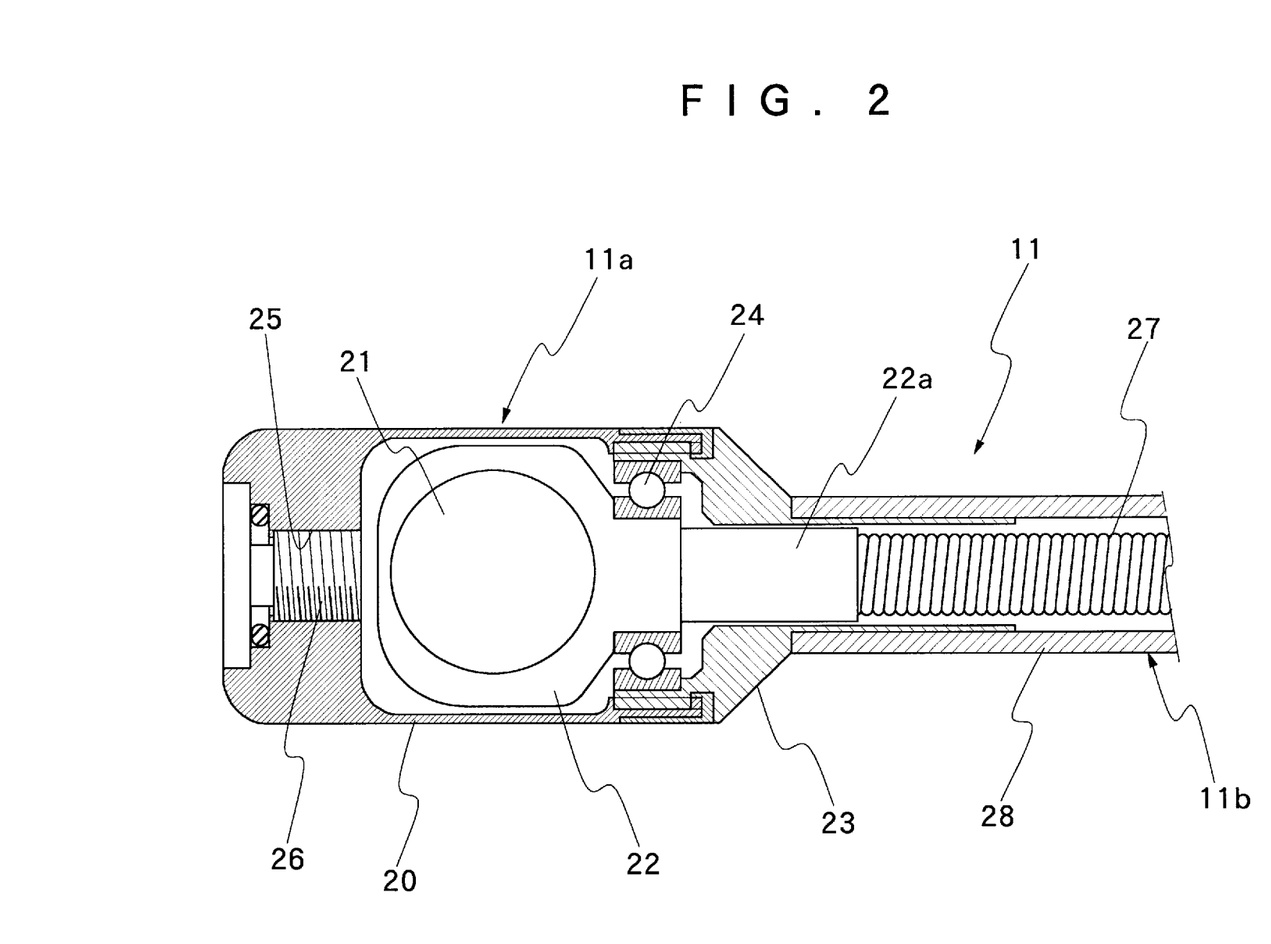
FIG. 2 is a schematic sectional view on an enlarged scale of a probe head which is connected to the fore distal end of an elongated flexible cord member of the ultrasound probe.

Shown in a sectional view in FIG. 2 is the manner in which the ultrasound probe head 11a is connected to the fore end of the flexible cord member 11b. The ultrasound probe head 11a is provided with an end cap 20 which is formed of a material with appropriate acoustic properties to accommodate an ultrasound transducer 21. The ultrasound transducer 21 is mounted on a rotatable base 22 which is rotatably supported through a bearing 24 on a connector tip 23 which is connected fluid-tight to the end cap 20 in such a manner as to serve also as a shape retainer for the latter. Provided in the distal end face of the end cap 20 is a tapped hole 25 to supply therethrough an ultrasound transmissive medium into the end cap 20. The tapped hole 25 is normally closed by a plug member 26 which is in the form of a male screw in the particular embodiment shown.

The rotatable base 22 is provided with a rotational shaft portion 22a which is extended rearward on the inner side of a cylindrical rear extension 23a of the connector tip 23. The proximal ends of the rotational shaft 22a and cylindrical rear extension 23a are extended into fore end portions of the cord member 11b and connected to a flexible shaft 27 and an outer flexible sheathing tube 28 of the cord member 11b, respectively. The flexible shaft 27 is, for example, in the form of a coil tube constituted by tightly wound helical metal-wire coils which are rotatable about the longitudinal axis of the cord member to transmit rotations to the rotatable base 22. A coaxial signal cable 29 (FIG. 3) to the ultrasound transducer 21 is passed through the flexible shaft 27. The outer flexible sheath 28 is made of soft synthetic resin material or the like.

As the flexible shaft 27 is turned about its longitudinal axis within the flexible sheath 28, its rotation is transmitted to the rotatable base 22 through its rotation shaft portion 22a. The ultrasound transducer 21, which is mounted on the rotatable base 22, is put in rotation with the latter at the time of radial scans, triggering ultrasound pulses and receiving reflected echo signals through the ultrasound transducer 21 at predetermined angular intervals.

Figure 3:
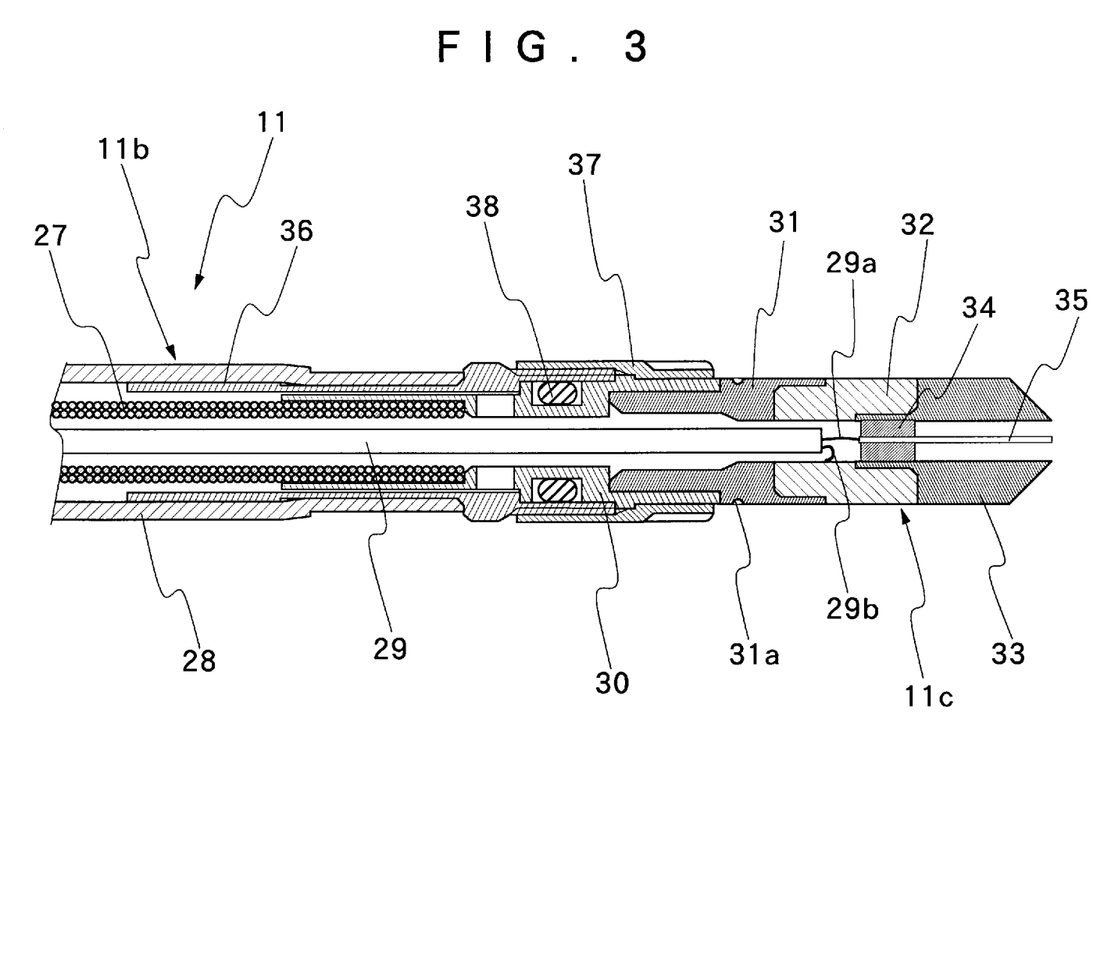
FIG. 3 is a schematic sectional view on an enlarged scale of a connector portion at the proximal end of the cord member.
Figure 4:
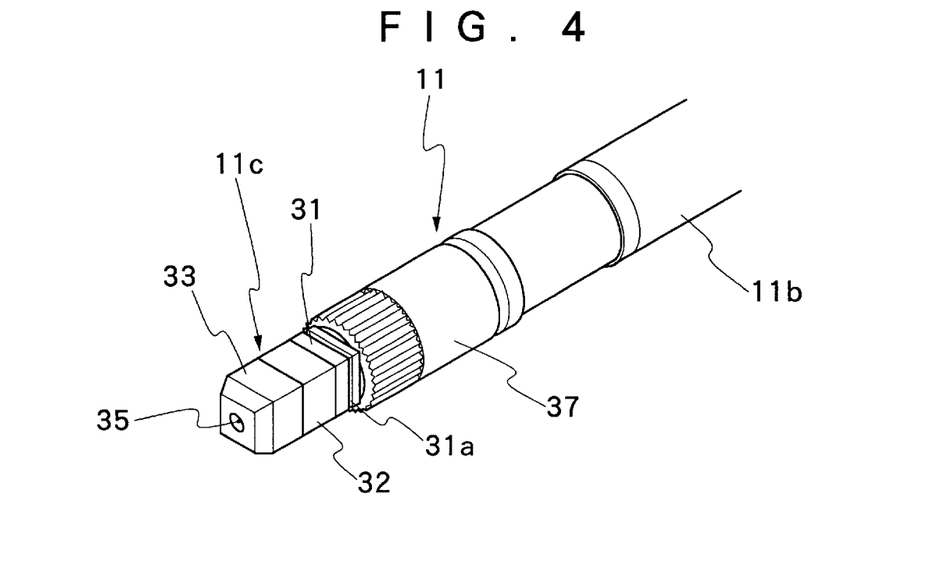
FIG. 4 is a schematic outer view of the connector portion of the cord portion shown in FIG. 3.

As shown particularly in FIGS. 3 and 4, the flexible cord member 11b is provided with a connector 11c at its proximal end. The connector 11c is largely constituted by a rotatable part and a fixed part. The rotatable part includes a rotary body 30 which is connected to the flexible shaft 27, a first insulating member 31, en electrode 32, and a second insulating member 33. All of these members of the rotatable part are formed in a hollow tubular shape and successively connected end to end by fitting or threaded engagement with each other. The coaxial signal cable 29 is passed through the internal hollow spaces of these rotating members, and its core and shield wires 29a and 29b are connected to an electrode pin 35, which is retained within the second insulating member 33 through a support ring 33, and an electrode 32, respectively. On the other hand, the fixed part of the connector includes an end ring 36 and a stopper ring 37. The end ring 36 is fitted in a proximal end portion of the sheath 28, with its inner periphery in sliding contact with the rotary member 30. In order to shield the sliding portions, a seal ring 38 is fitted on the rotary member 30. The stopper ring 37 is fixedly threaded on the end ring 36, and its circumferential surface is knurled with axial grooves.

Figure 5:
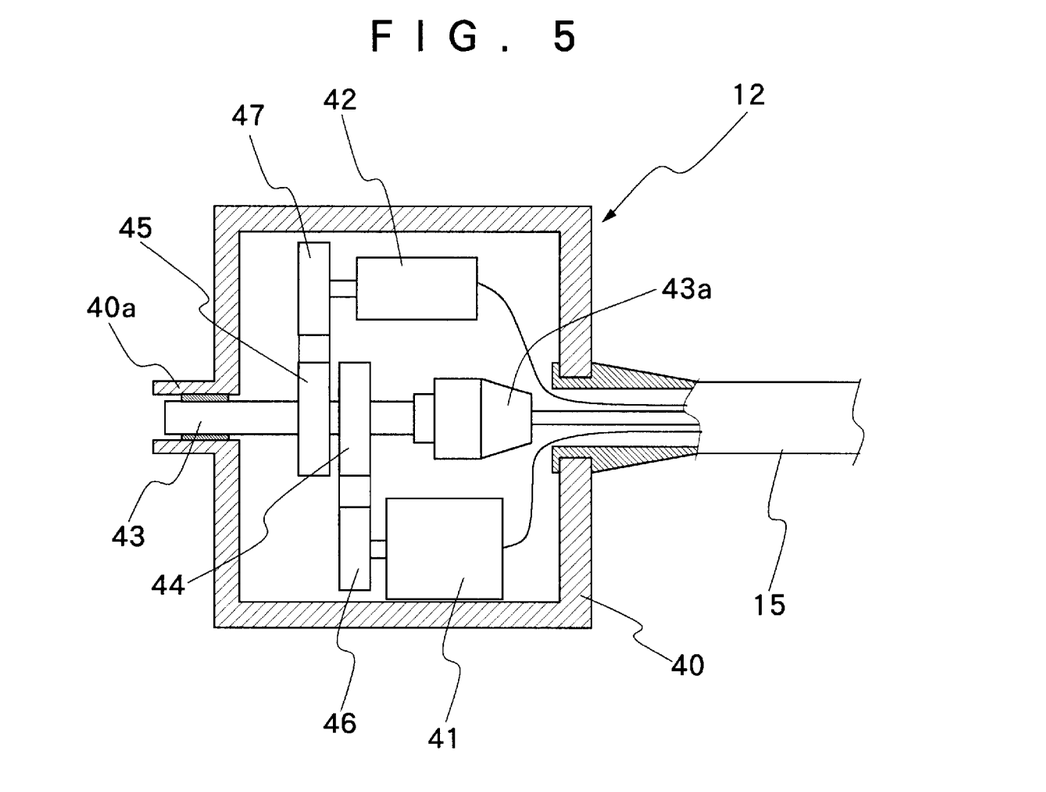
FIG. 5 is a schematic sectional view of a manipulating control head of the ultrasound probe.
Figure 6:
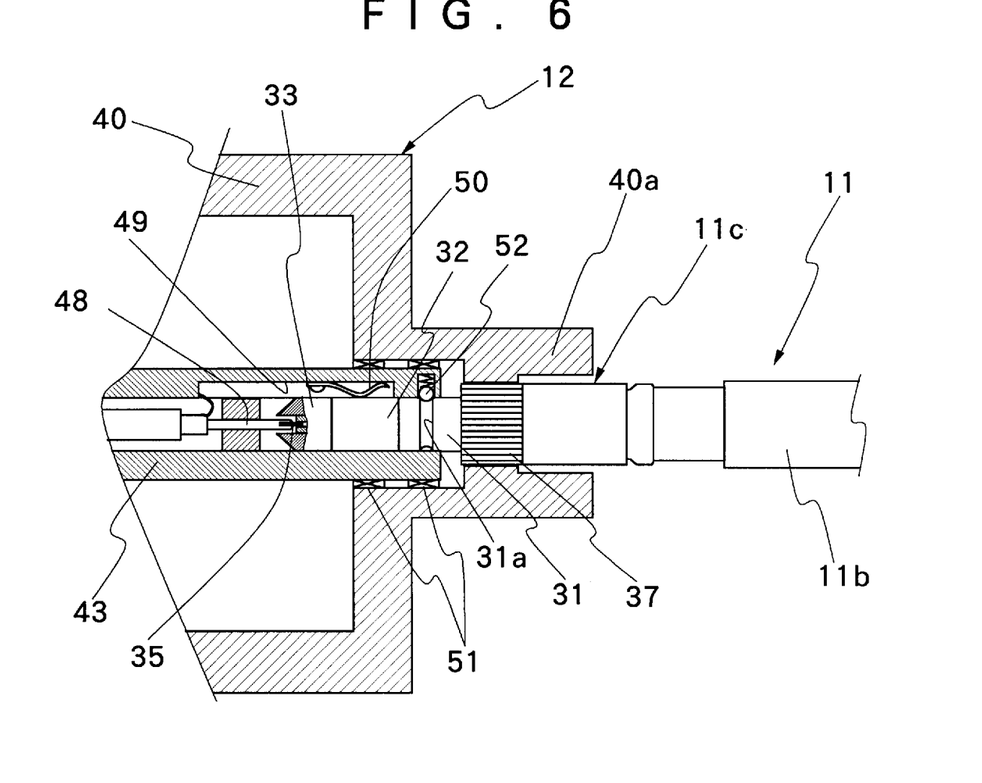
FIG. 6 is a schematic sectional view on an enlarged scale of a connector portion which connects the proximal end of the cord member to the manipulating control head.

As shown in FIGS. 5 and 6, the connector section 11c is plugged into a casing 40 of the probe controller unit 12, which has the afore-mentioned cable 15 led out from the opposite side of the casing 40. The casing 40 houses therein a motor 41 serving as a rotational drive means, and an encoder 42 serving as a rotational angle detector. A rotational shaft 43 which is driven by the motor 41 is partly projected on one side of the casing 40. A couple of gears 44 and 45 are mounted on the rotational shaft 43, of which the gear 44 is meshed with a gear 46 of the motor 41 while the other gear 45 is meshed with a gear 47 of the encoder 42. Provided at the inner end of the rotational shaft 43 is a rotary connector 43a which includes a rotary electrode and a stationary electrode thereby to transmit signals from the rotational shaft 43 to the non-rotatable cable 15.

Rotating and stationary members on the part of the connector section 11c at the proximal end of the ultrasound probe 11 are connected to the rotational shaft 43 and the casing 40 on the part of the probe controller unit, respectively. The casing 40 is provided with a cylindrical socket 40a around the projected rotational shaft 43. When plugged in, the axial grooves of the knurled circumferential surface of the stopper ring 37 of the connector section 11c are brought into splined engagement with the inner periphery of the socket 40a to block rotation of the stationary member and the sheathing tube 28. The rotational shaft 43 is of a hollow structure having a square open cavity. On the other hand, as shown particularly in FIG. 4, the first insulating member 31 and electrode 32 of the connector section 11c are formed in a square shape correspondingly to the shape of the internal cavity of the rotational shaft 43. The second insulating member 33 at the distal end of the connector section 11c is formed in the shape of truncated pyramid. Accordingly, rotation of the rotational shaft 43 is followed by the rotating members of the connector section 11 and thereby transmitted to the flexible shaft 27.

Thus, the probe controller unit 12 functions as a signal relay means. For this purpose, a pin 48 is projected in the internal cavity of the rotational shaft 43 for engagement with the electrode pin 35 on the side of the connector 11. Further, a recessed portion 49 is provided in the internal cavity of the rotational shaft 43 to accommodate a spring contact 50, which is brought into abutting contact with a circumferential surface of the electrode 32 to make an electrical connection therewith when the connector section 11c is plugged in. In this connection, shown at 51 in FIG. 6 is a bearing which rotatably supports the rotational shaft 43 within the cylindrical socket 40a, and at 52 is a click mechanism which releasably holds the connector section 11c in the plugged position by engagement with an annular groove 31a which is provided on the circumference of the first insulating member 31.

With the arrangements just described, the connector section 11c is plugged in the socket 40a on the probe controller unit 12 to connect the ultrasound probe to the ultrasound image observation terminal 13. Then, a power switch of the ultrasound image observation terminal 13 is turned on to start the motor 41. Consequently, the rotation of the motor 41 is transmitted to the rotary base 22 on the probe head 11a through the flexible shaft 27 to put the ultrasound transducer 21 in rotation. In a radial scan, while detecting the angular position of the ultrasound transducer 21 by the encoder 42, ultrasound pulse signals are triggered at: predetermined angular intervals to receive echo signals from various internal body tissues.

The ultrasound probe 11 is provided with a bulged probe head 11a at its distal fore end, which is larger in diameter than the instrument channel 6 on the endoscope, for the purpose of securing in the end cap 20 a space which is broad enough for accommodating the ultrasound transducer 21 of a large size. As mentioned hereinbefore, an ultrasound transducer with a broader active surface can transmit low-frequency high-power ultrasound pulses and has higher signal receptivity to improve the quality of ultrasound images which will be obtained by processing return echo signals.

The use of the ultrasound transducer 21 of a large size, however, results in bulkiness of the probe head 11a which is difficult to pass through the instrument channel 6 of the endoscope 1. According to the present invention, except the bulky probe head 11a, the remainder of the ultrasound probe 11, including the cord member 11b and connector section 11c, is formed in a diameter smaller than the inside diameter of the instrument channel 6 of the endoscope 1. Therefore, the ultrasound probe 11 according to the present invention is placed in the endoscopic instrument channel 6 in an inverse fashion, that is to say, not from its fore end with the probe head 11a but from its proximal end with the connector section 11c and not through the approach way 5 on the manipulating head grip of the endoscope 1 but through the exit opening of the instrument channel 6 at the fore distal end of the endoscopic insertion rod 3. Namely, the connector section 11c of the ultrasound probe 11 is advanced into the instrument channel 6 through the opening at the fore distal end of the endoscopic insertion rod 3 and drawn out through the approach way 5 on the manipulating head grip of the endoscope 1 for connection to the probe controller unit 12. The ultrasound probe 11 is placed in the endoscopic instrument channel 6 in this manner prior to introducing the endoscopic insertion rod 3 into a body cavity.

Thus, it has become possible for the probe head 11a to employ the ultrasound transducer 21 of a large size as described above, freed from the dimensional limitations as normally imposed in relation with the inside diameter of the endoscopic instrument channel 6. However, the size of the probe head 11a is subject to limitations relating to the thickness of the endoscopic insertion rod 3. If the probe head 11a is larger than the outside diameter of the endoscopic insertion rod 3, it will become difficult to introduce the endoscope into constricted narrow canals which may exist on the way to a body cavity to be examined, in addition to a problem that the illumination and observation windows 7 and 8 of the endoscope could be completely blocked by the probe head 11a. Therefore, the probe head 11a should be increased in size within a range in which it would not bulge out on the opposite sides of the endoscopic insertion rod nor would it block the endoscopic illumination and observation means at the distal end of the insertion rod 3.

Figure 7:
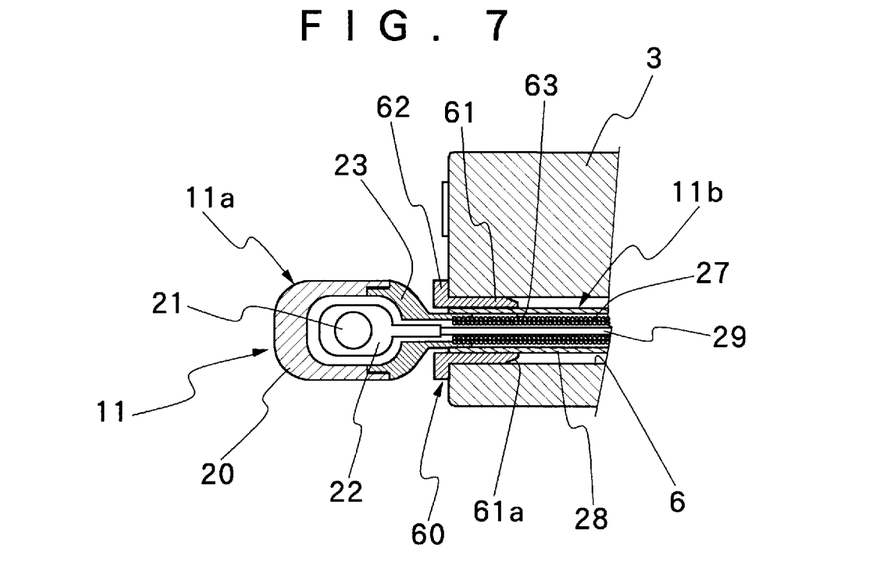
FIG. 7 is a schematic sectional view of the scanner portion of the ultrasound probe, which is fixed in an exit opening at the fore distal end of an endoscopic instrument channel.

When the ultrasound probe 11 is placed in the endoscope 1, the probe head 11a is normally protruded by a certain length from the fore end of the endoscopic instrument channel 6. The probe head 11a is connected to the fore end of a flexible cord member 11b which is thinner than the inside diameter of the endoscopic instrument channel 6, so that, if left in a free state, it tends to flex or bend in arbitrary directions. Shown in FIGS. 7 and 8 is a probe head holder member 60 which is employed in this embodiment to hold the probe head 11a fixedly at the fore distal end of the endoscopic instrument channel 6.

The probe head holder member 60 is formed of a resilient material like rubber and constituted by a cylindrical body 61 providing an axial through passage 63, and a flange portion 62 formed at one end of the cylindrical body 61. The circumferential surface of the cylindrical body 61 of the probe head holder member 60 is tapered off at the other end away from the flange portion 62 to provide a pilot portion 61a. The cylindrical body 61 of the probe head holder member 60 is formed to have an inside diameter which is larger than the outside diameter of the flexible cord member 11b but smaller than or equivalent with the outside diameter of a neck portion of the connector piece 23 of the ultrasound probe head 11a. Therefore, the neck portion of the connector piece 23, of the ultrasound probe head 11a can be fitted in the probe head holder member 60 substantially in a tightly sealed state. The probe head holder member 60 is either separably connected to the ultrasound probe head 11a or fixedly connected to the latter by the use of an adhesive. The cylindrical body 61 of the probe head holder member 60 is formed to have an outside diameter slightly smaller than the inside diameter of the opening at the fore distal end of the instrument channel 6. The outside diameter of the flange portion 62 of the probe head holder member 60 is same as or smaller than that of the ultrasound probe head 11a.

Figure 8:
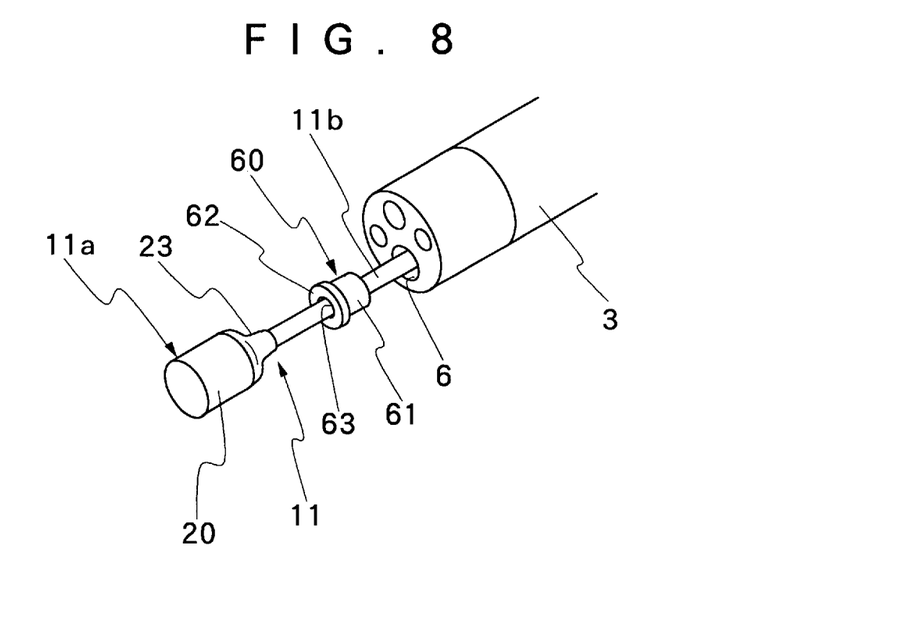
FIG. 8 is a schematic perspective view of the scanner portion of the ultrasound probe, which is protruded forward away from the endoscopic instrument channel.

The probe head holder member 60 is put on a fore end portion of the cord member 11b immediately behind the probe head 11a, with the flange portion 62 faced toward the probe head 11a as shown particularly in FIG. 8. After putting the probe head holder member 60 on, the connector section 11c at the proximal end of the ultrasound probe 11 is drawn out through the approach way 5 and plugged into the probe controller unit 12. On the other hand, the probe head holder member 60 is fitted into the distal opening of the endoscopic instrument channel 6 up to the flange portion 62. Since the probe head holder member 60 is formed of a resilient material as mentioned hereinbefore, it is gripped in a compressed state between the inner periphery of the instrument channel 6 and a circumferential surface of the connector section 23 of the ultrasound probe head 11a. Accordingly, the probe head 11a is fixedly retained at the fore end of the instrument channel 6 by the resilient force of the probe holder member 60. When the endoscopic insertion rod 3 is introduced into a body cavity, the ultrasound probe head 11a, which is projected from the fore distal end of the endoscopic insertion rod 3, is retained stably in a fixed state without hindering the movements of the endoscope. Therefore, even when used in assembly with the ultrasound probe 11, the endoscope 1 can be operated smoothly through constricted canals or the like at the time of insertion into a body cavity, not to mention the effects of lessening pains on the part of the patient.

Once the endoscopic insertion rod 3 is advanced to an aimed position within a body cavity, the ultrasound probe head 11a is put in a position for an ultrasound examination, and this can be done from the side of the endoscopic insertion rod 3. Namely, by the use of a flexible angle section which is usually provided on the insertion rod 3 for bending or flexing a fore end portion of the insertion rod 3, the ultrasound probe head 11a can be turned into desired direction, in addition to adjustments in axial position by pushing in or pulling out the whole endoscopic insertion rod 3 within the body cavity to bring the ultrasound transducer accurately to a suitable position for scanning a target spot or area. Although the ultrasound probe head 11a is fixed on the endoscopic instrument channel 6 through the probe head holder member 60, the end cap 60 which houses the ultrasound transducer element 21 is projected on the front side of the flange portion 62 of the probe head holder member 60 to preclude the possibilities of the holder member 60 coming into the way of ultrasound signal transmission and reception in radial scan operations by the ultrasound transducer 32.

When the probe head holder member 60 is fitted to hold the ultrasound probe head 11a in a fixed state at the distal end of the endoscopic insertion rod 3 as described above, the instrument channel 6 is blocked by the holder member 60 in such a way as to exclude other use of the instrument channel 6, which is normally utilized also for feeding deaerated water into a body cavity as ultrasound transmissive medium at the time of ultrasound examination. Therefore, the ultrasound probe of this embodiment is suitable for use with an endoscope which is provided with another instrument channel which can be used for the supply of deaerated water, in addition to the instrument channel 6 in which the ultrasound probe 11 is placed.

Alternatively, the probe head holder member 60 may be provided fixedly on the ultrasound probe head 11a and arranged to engage in the endoscopic instrument channel 6 with such a degree of looseness that it will come off the instrument channel 6 when a proximal end portion of the ultrasound probe 11 is pushed in by the operator, permitting to use the instrument channel for the supply of deaerated water. In this connection, the ultrasound probe head 11a is required to be in a stabilized state at least during introduction into a body cavity of the endoscopic insertion rod 3. When introducing the insertion rod 3 into a body cavity, the ultrasound probe head 11a is subjected to resistive forces which tend to push the probe head 11a into the endoscopic instrument channel 6. Accordingly, during introduction of the endoscopic insertion rod 3, there is no possibility of the ultrasound probe head 11a coming off the instrument channel 6 as long as the probe head holder member 60 is gripped in the instrument channel 6 in a slightly compressed state by fitting engagement with the latter. Thus, as soon as the endoscopic insertion rod reaches an aimed position within a body cavity, the ultrasound probe head 11a can be put off to use the instrument channel 6 for the supply of deaerated water. After feeding a required quantity of deaerated water, the probe holder member 60 which is fixed on the ultrasound probe head 11a can be withdrawn once again into the instrument channel 6 by pulling the flexible cord member 11b of the probe 11 from the side of the approach way 5. In doing so, thanks to the provision of the tapered pilot portion 61a on the cylindrical body 61, the probe head holder member 60 can be smoothly withdrawn into the instrument channel 6 of the endoscope 1.

Figure 9:
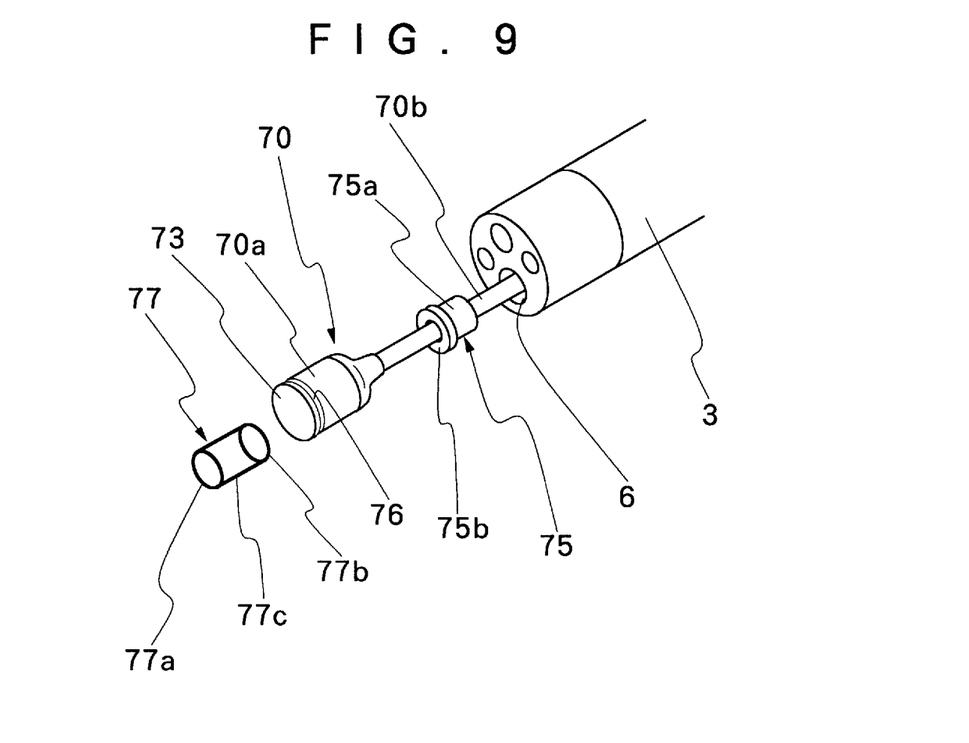
FIG. 9 is a schematic perspective view of the ultrasound probe head, and a balloon anchor for hermetically fixing a balloon on the ultrasound probe head before fixing same at the distal end of an endoscopic insertion rod.
Figure 10:
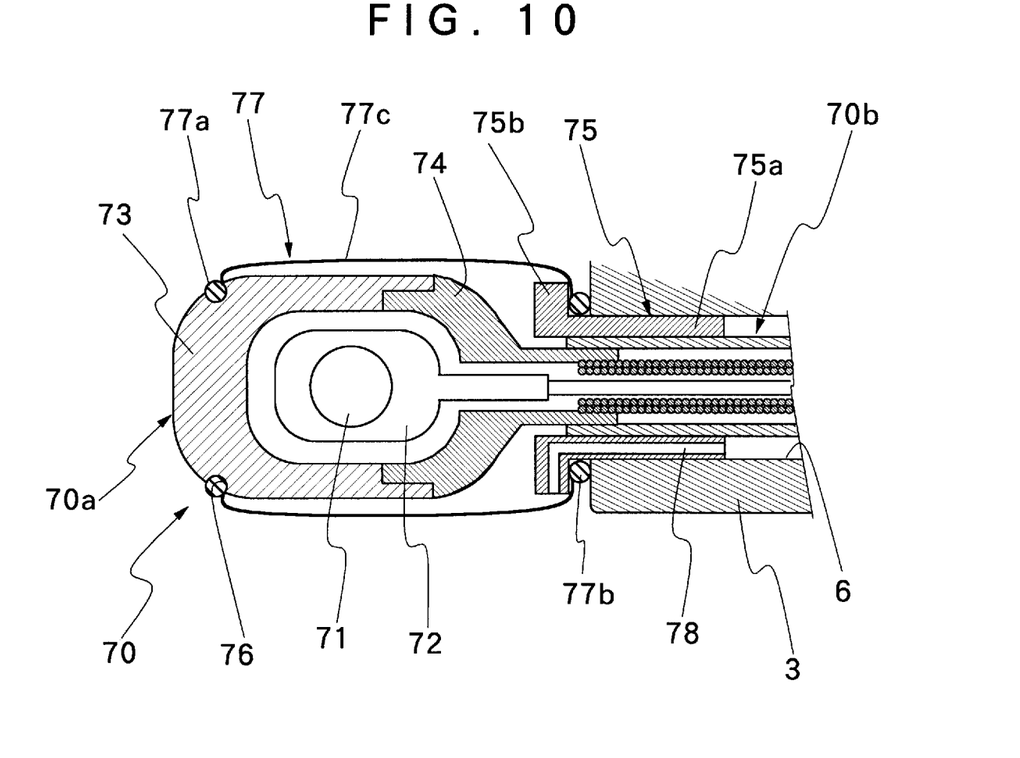
FIG. 10 is a schematic sectional view on an enlarged scale of the ultrasound probe head which is fitted with a balloon and releasably fixed to an endoscopic insertion rod.

In ultrasound examinations, a balloon is fitted on the ultrasound probe head 11a for the purpose of suppressing to a minimum the attenuation of ultrasound signals as caused by intervention of air between the ultrasound transducer and an intracavitary wall and for securing a suitable stand-off distance from an intracavitary wall. In some cases, an ultrasound transmissive medium is charged into a balloon of this sort, bring the latter into an inflated state. FIGS. 9 and 10 show another embodiment having means for anchoring a balloon on the probe head.

In these figures, indicated at 70 is an ultrasound probe which is similarly provided with an ultrasound probe head 70a at the fore distal end of a flexible cord member 70b. In a manner similar to the foregoing first embodiment, the probe head 70a has an ultrasound transducer 71 is mounted on a rotatable base 72 within an end cap 73 which is securely connected to a sheathing tube of the flexible cord member 70b through a connecting portion 74. Fitted on the connecting portion 74 is a probe head holder member 75 which is formed of resilient material like rubber.

A balloon 77 is fitted on the ultrasound probe head 70a between an annular groove 76, which is formed around the circumference of a fore end portion of the end cap 73 of the probe head 70a, and a cylindrical body portion 75a immediately behind a flange portion 75b of the probe head holder member 75. The balloon 77 consists of a flexible tubular membrane 77c and has its opposite ends hermetically stopped in position on the ultrasound probe head 70a and the probe head holder member 75 by stopper rings 77a and 77b, respectively. The balloon 77 is inflated to a predetermined degree upon supplying thereinto an ultrasound transmissive medium like deaerated water. For the supply of deaerated water into the balloon 77, a fluid passage 78 is bored through the probe head holder member 75. The fluid passage 78 has its one end opened on the inner end face of the cylindrical body portion 75a and the other end opened on the circumference of the probe head holder member 75. In this respect, there is no possibility of a supplied fluid spilling out around the probe head holder member 75 which is hermetically fitted in the endoscopic instrument channel 6. Accordingly, upon feeding deaerated water into the endoscopic instrument channel 6, supplied water is allowed to flow into the probe head 70a on the inner side of the flexible membrane 77c of the balloon 77 through the fluid passage 78, causing the flexible membrane 77c to inflate to a predetermined extent.

The balloon 77 stays in a contracted or deflated state until the endoscopic insertion rod 3 has been introduced into a body cavity, and inflated by feeding thereto a predetermined quantity of deaerated water prior to ultrasound examination. Therefore, the inflated flexible membrane 77c of the balloon 77 is abutted against an intracavitary wall to keep the ultrasound transducer 71 at a suitable stand-off distance from the intracavitary wall during transmission and reception of ultrasound signals. Consequently, the balloon 77 contributes to suppress attenuation of ultrasound signals and to secure a stand-off distance for the purpose of preventing reception of multiple echoes.

Figure 11:
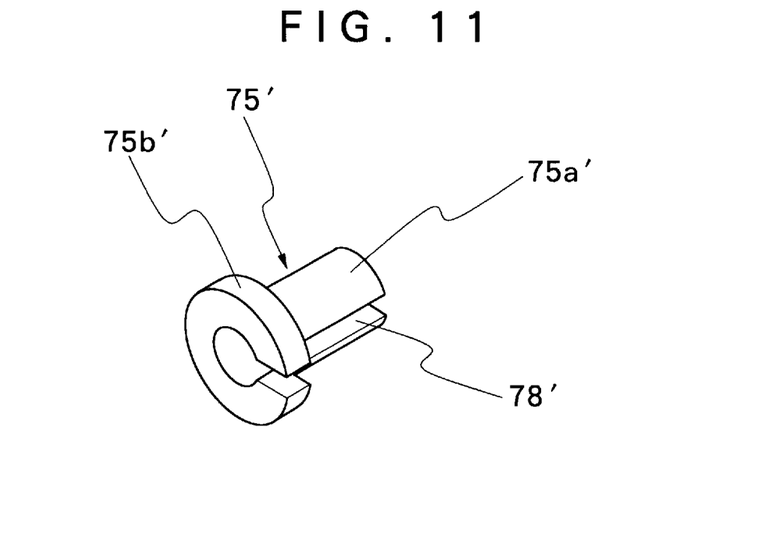
FIG. 11 is a schematic outer view of a balloon anchor means.

Since the balloon 77 is anchored in position on the ultrasound probe head 70a by the stopper rings 77a and 77b, there may be employed a split type probe head holder member 75' which is provided with an axial split groove as shown in FIG. 11. In this case, the probe head holder member 75', which is fitted on the connecting neck portion of the probe head 70a, is held in engagement with the latter by fitting the stopper ring 77a in the annular groove 76 on the end cap 73 of the probe head 70a while fitting the other stopper ring 77b on a cylindrical body portion 75a' of the probe holder member 75 immediately behind its flange portion 75b'. This split type probe head holder member 75' can be used for other ultrasound probes which differ in outside diameter of the connecting neck portion 74. In case the split groove 78' in the cylindrical body portion 75a' of the probe head holder member 75' remains open when fitted in the endoscopic instrument channel 6, it can be used as a fluid passage 78' in feeding an ultrasound transmissive medium to the balloon 77. The stopper ring 77b, if gripped between the flange portion 75b' of the probe head holder member 75 and the fore end face of the endoscopic insertion rod 3, can suitably function to prevent spill-out of the ultrasound transmissive medium. For this purpose, at the time of fitting the probe head holder member 75' into the endoscopic instrument channel 6, the flange portion 75b' should be pushed against the fore end face of the endoscopic insertion rod 3 to grip the stopper ring 77b' of the balloon 77 tightly therebetween. By so doing, the stopper ring 77b' can function as a seal ring which shields off the fluid passage 78' which might otherwise be communicated with the outside.

Referring now to FIGS. 12 through 15, there is shown another embodiment in which, instead of the probe head holder members as described above, a hood member 80 is fitted in the opening at the distal end of the endoscopic instrument channel in such a way as to function also as a probe head holder member.

Figure 12:
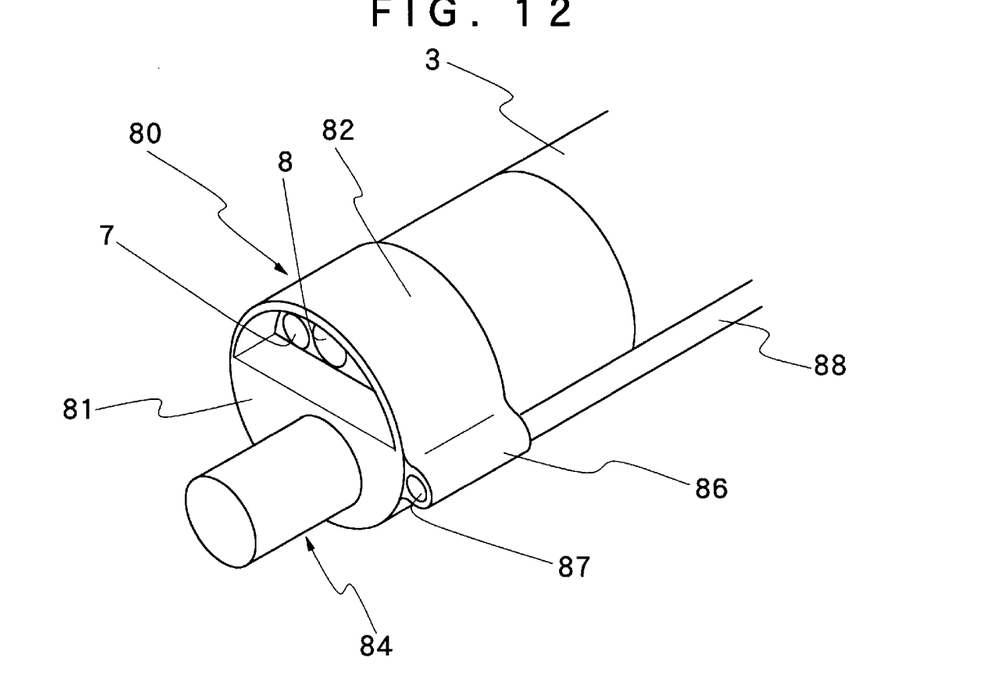
FIG. 12 is a schematic perspective view on an enlarged scale of the ultrasound probe head releasably fixed on an endoscopic insertion rod by the use of a different probe head holder means.
Figure 14:
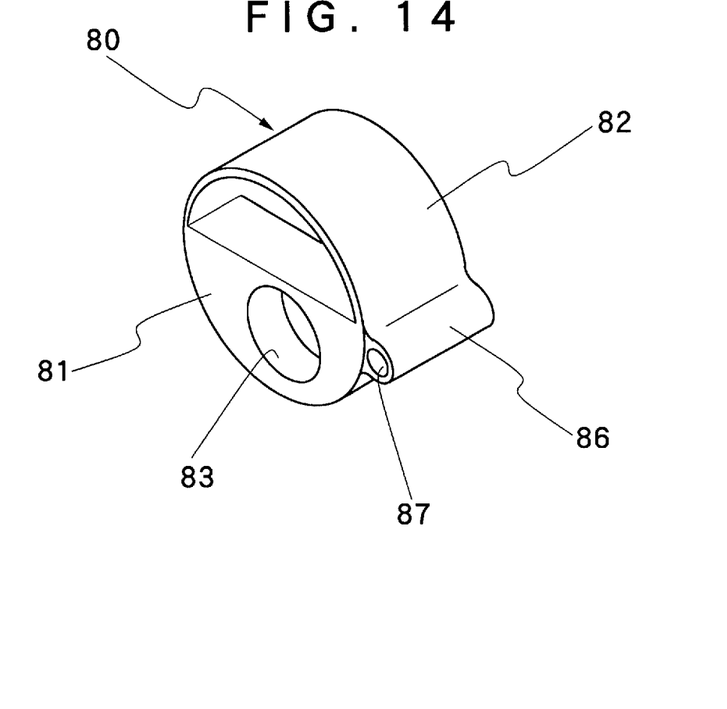
FIG. 14 is a schematic perspective view of the hood member, taken from the front side thereof.
Figure 15:
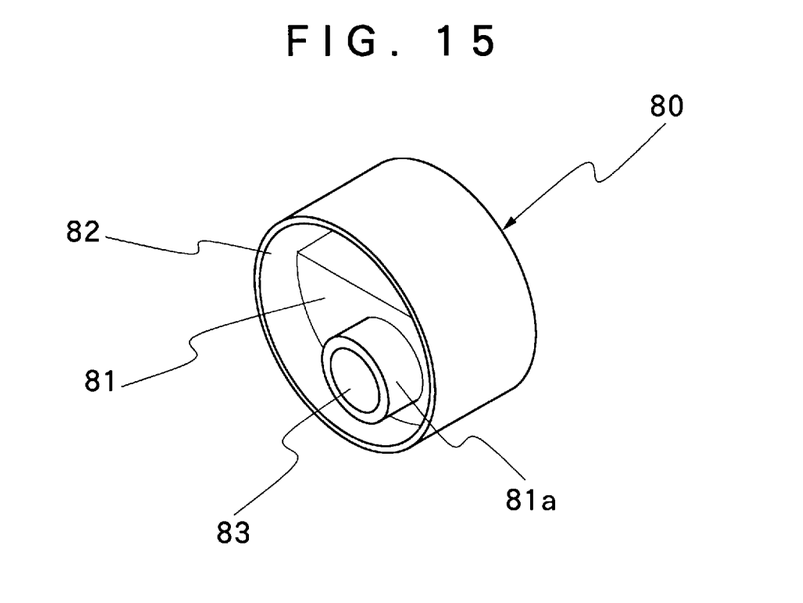
FIG. 15 is a schematic perspective view of the hood member, taken from the rear side thereof.

More particularly, the hood member 80 is formed of a resilient material like rubber, and provided with a probe head holder portion 81 of substantially semi-circular shape. Formed integrally with and around the probe head holder portion 81 is a ring-like girdle portion 82 with an inside diameter smaller than the outside diameter of an endoscopic insertion rod 3. When the girdle portion 82 is fitted on a distal end portion of the insertion rod 3, the hood member 80 tightly grips the endoscopic insertion rod 3 by its resilient force with the probe head holder portion 81 in abutting engagement with the distal end face of the insertion rod 3. When the hood member 80 is fitted on the insertion rod 3, the opening at the distal end of the endoscopic instrument channel 6 is covered under the probe head holder portion 82 but endoscopic illumination and observation means 7 and 8 on the insertion rod 3 remain uncovered state since the end face of the hood member 80 is open in its upper half.

Figure 13:
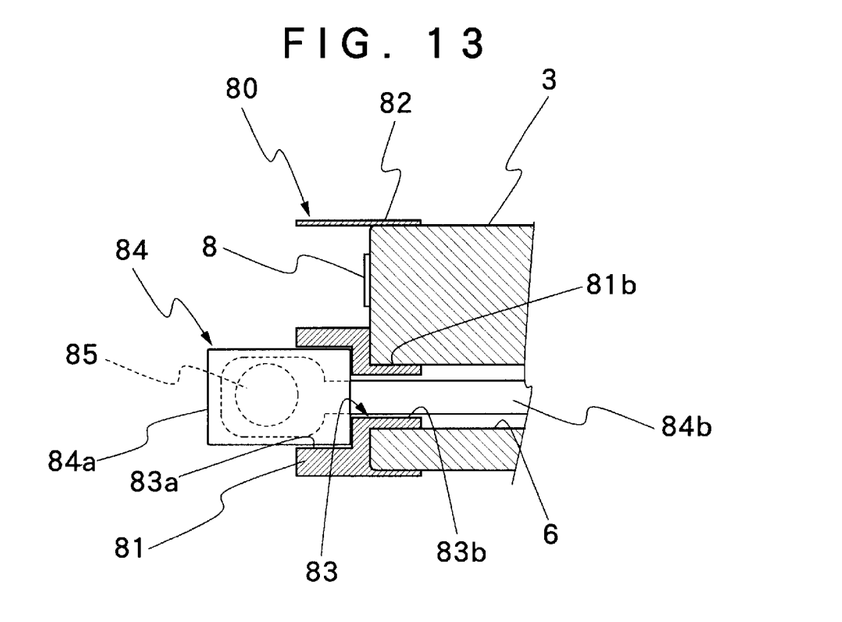
FIG. 13 is a schematic sectional view of a hood member in the position of FIG. 12.

As shown particularly in FIG. 13, the probe head holder portion 81 is provided with a tubular projection 81a on the inner side facing the instrument channel 6 on the endoscopic insertion rod 3. The tubular projection 81a has an outside diameter which substantially corresponds to the inside diameter of the instrument channel 6 on the endoscope 1. Besides, the probe head holder portion 81 is provided with a hollow body with an internal cavity 83 of a stepped form in the axial direction. The internal cavity 83 is open at the opposite ends, and includes a large diameter portion 83a, which is located on the front side, and a small diameter portion 83b coextensive with the tubular projection 81a.

Indicated at 84 is an ultrasound probe which is constituted by an ultrasound probe head 84a of a cylindrical shape and a flexible cord member 84b which is connected directly to the cylindrical probe head 84a. The ultrasound probe head 84a is arranged to have an outside diameter slightly larger than the large-diameter portion 83a of the inner cavity 83 of the probe head holder portion, while the flexible cord member 84b is arranged to have an outside diameter smaller than the small-diameter portion 83b of the internal cavity 83. Further, the large-diameter portion 83a is arranged to have the smallest possible depth in stably holding the ultrasound probe head 84a on the hood member 80, namely, should be shallow enough to keep the ultrasound transducer 85 of the probe head 84 out of the cavity 83.

Further, the hood member 80 is provided with a hollow protuberance or rib 86 axially along one side thereof, providing a through passage 87 to be connected to a side channel 88 which is provided along one side of the endoscopic insertion rod 3. Of course, there is no need for providing the passage 87 and side channel 88 in case the endoscopic insertion contains a plural number of instrument channels. Namely, in case the endoscopic insertion rod 3 contains another or second instrument channel, it is desirable to provide a through passage or another open cavity in the probe head holder portion 81 in direct communication with the second instrument channel.

In use, the flexible cord member 84b is inserted into the cavity 83 of the probe head holder portion 81 of the hood member 80 from the front side, that is, from the side of the large-diameter portion until the ultrasound probe head 84a is fixed on the hood member 80 by intimate fitting engagement with the large-diameter portion 83 of the cavity 83. In this state, the connector section at the proximal end of the flexible cord member is inserted into the instrument channel 6 through its opening at the fore distal end of the insertion rod 3, and then the girdle portion 82a of the hood member 80 is put on distal end of the insertion rod 3 in such a way that the tubular projection 81a of the probe head holder portion 81 is fitted in the endoscopic instrument channel 6. If necessary, the side channel 88 on the endoscopic insertion rod 3 is connected to the axial through passage 87 on the hood member 80. As a result, the ultrasound probe head 84a, which is projected from the distal end of the instrument channel 6, is retained in a stabilized state on the holder portion 81 of the hood member 80, ensuring smooth insertion into a body cavity of the endoscope 1 and lessening pains on the part of the patient, despite the use of the ultrasound probe head 84a of a large size.

Figure 16:
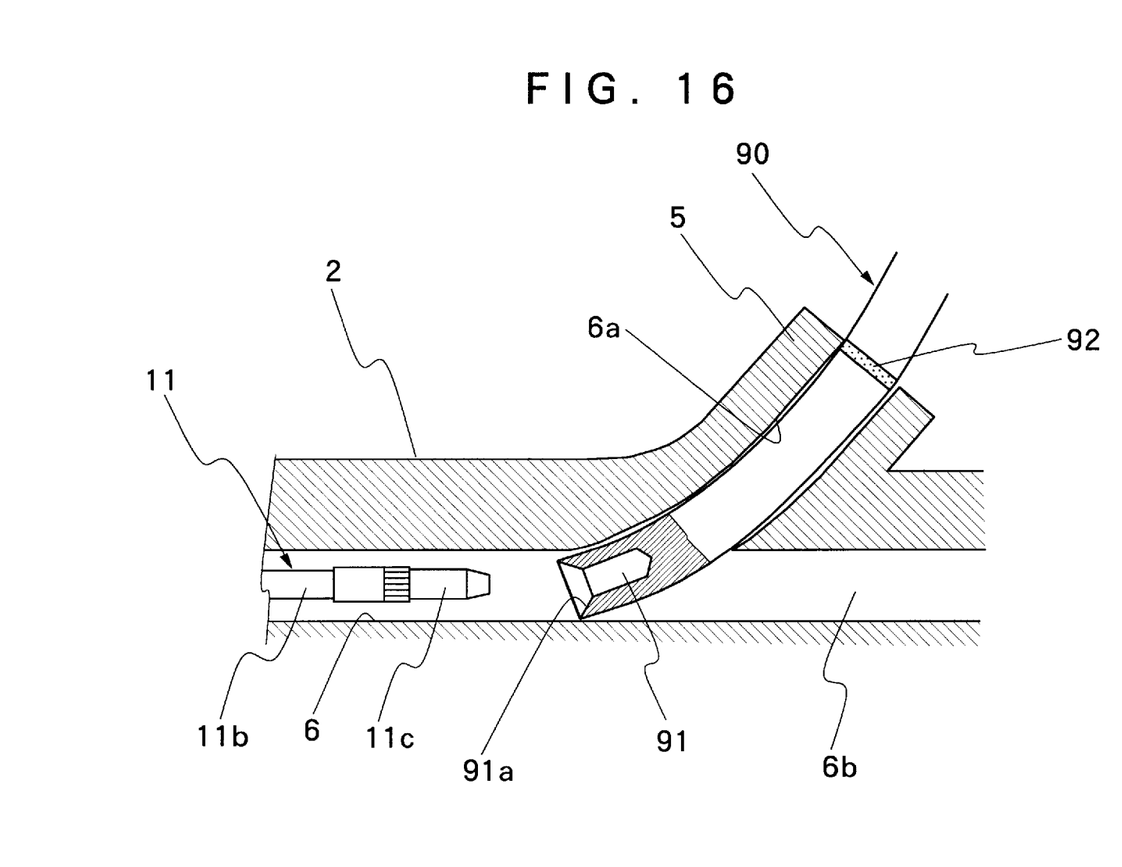
FIG. 16 is a schematic sectional view of a probe guide member for guiding a connector section at the proximal end of a cord member out of an instrument channel of an endoscope.

The endoscopic instrument channel 6 is bifurcated into two branch passages within the manipulating head grip 2, i.e., into a passage 6a leading to the afore-mentioned approach way 5 and a passage 6b which is usually used as a suction passage. As the ultrasound probe 11 is placed in the endoscopic instrument channel 6 inversely from its tail end, that is, from the connector section 11c at its proximal end, it could be mistakenly led into the suction passage 6b instead of the passage 6a to the approach way 5. Problems of this sort can be avoided by the use of a guide member 90 as shown in FIG. 16, which is adapted to guide the connector section 11c at the leading end of the flexible cord member 11b toward the approach way 5 of the instrument channel 6 in an assured manner. As described hereinbefore, the first insulating member 31, electrode member 32 and second insulating member 33 are successively projected in the connector section 11c. The second insulating member 33 is formed in a truncated-pyramid shape, while the ensuing electrode member 32 and first insulating member 31 are formed in the shape of a prism, and the stopper ring 37 in a circular shape. Taking into consideration stepwise variations in the surface contour of the proximal end portion of the connector section 11c, the guide member 90 formed of a material with both flexibility and stiffness and provided with an open recess or socket 91 in its head portion. The socket 91 is tapered off as indicated at 91a in inner peripheral edge portions around the outer open end of the socket 91.

The guide member 90 is introduced into the endoscopic instrument channel 6 through the approach way 5 and passage 6a a little ahead of a branching point where the instrument channel is branched into two passages 6a and 6b. The guide member 90 which has been introduced into the approach way 5 is invariably allowed to proceed to the instrument channel 6 through the passage 6a which is arranged to merge into the instrument channel 6 through a moderate curve line, with no possibilities whatsoever of the guide member 90 straying into the passage 6b which lies in the inverse direction or at an acute angle with the passage 6a. Further, the guide member 90 is preferred to have an outside diameter which is smaller than but as close as possible to the inside diameter of the endoscopic instrument channel 6. Preferably, a mark 92 is put on the circumference of the guide member 90 in such a position that it comes to the entrance of the approach way 5 when the fore end of the guide member 90 reaches a predetermined standby position in the instrument channel 6 past the above-mentioned branching point to the passage 6a.

On the other hand, the connector section 11c of the ultrasound probe 11 is inserted into the instrument channel 6 through the opening at the fore distal end of the endoscopic insertion rod 3 to meet the guide member 90 in the standby position. Upon meeting the guide member 90, the connector section 11c is pushed into the socket 91 through the tapered portion 91a at the entrance to the socket 91 and coupled with the latter. As the flexible cord member 11b of the probe 11 is further pushed into the instrument channel 6, the connector member 90, which is in a free state, is pushed back into and finally out of the approach way 5, guiding the connector section 11c of the probe 11 smoothly and securely into the passage 6a and then into the approach way 5 past the branching point to the passage 6b. Once the connector section 11c is led into the approach way 5, it can be easily pushed out through the opening at the entrance of the approach way 5.

Figure 17:
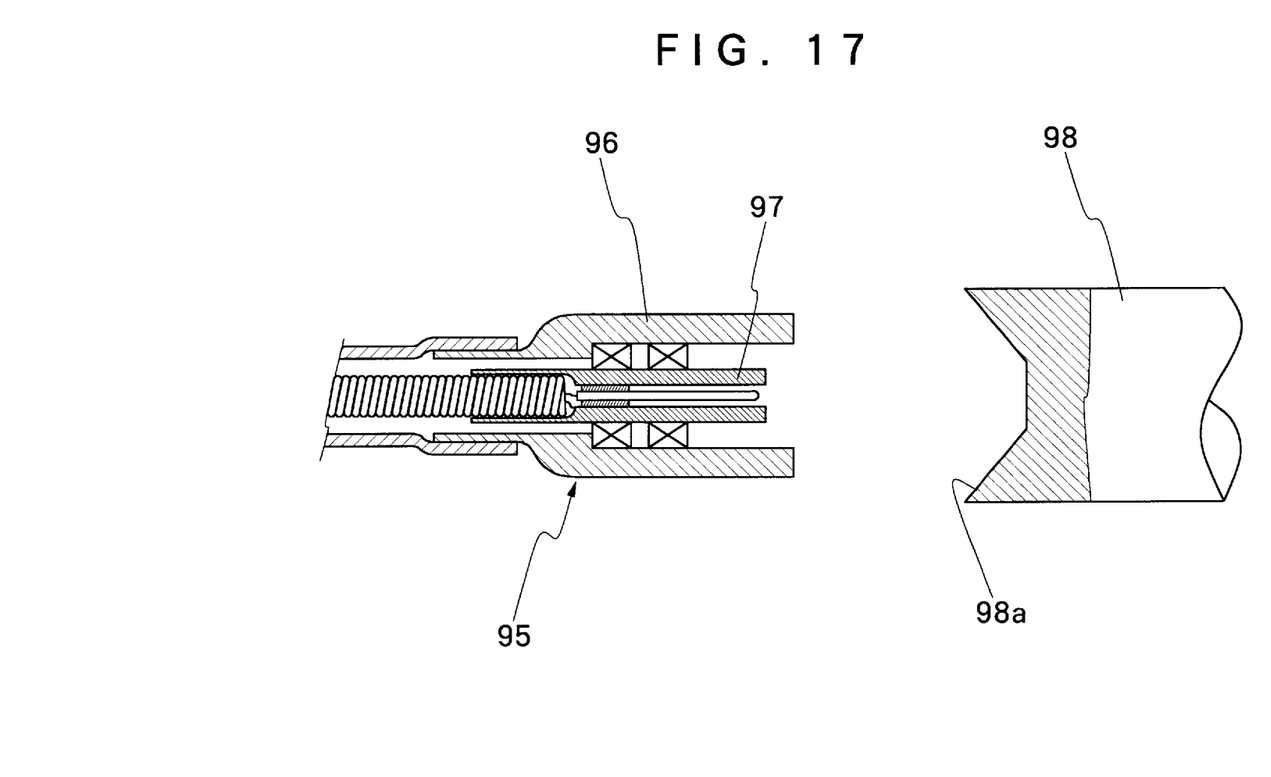
FIG. 17 is a schematic sectional view of another example of the probe guide member.
Figure 18:
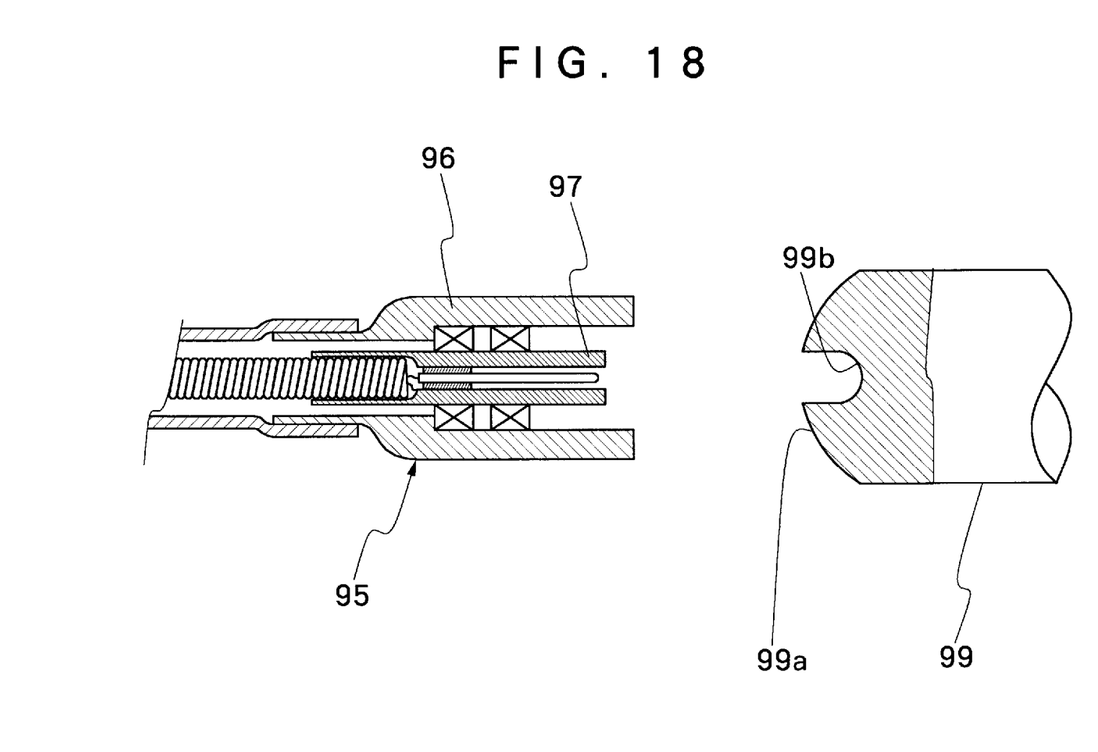
FIG. 18 is a schematic sectional view of still another example of the probe guide member.

With regard to the connector section 11c at the proximal end of the ultrasound probe 11, it does not necessarily have electrode members in a projected state as described hereinbefore. On the other hand, the guide member 90 is not necessarily required to hold the connector section by fitting engagement therewith, that is, if suffices for the guide member to be able to hold the connector section against deviating movements in directions perpendicular to the axis of the instrument channel. Shown in FIG. 17 is a connector section 95 of different construction, having a stopper ring 96 projected around and rearward of a rotating member 97. In this case, there may be employed a guide member 98 which is provided with a holder recess 98a having an inwardly converging tapered wall for abutting engagement with the projected stopper ring 96 of the connector section 95. Alternatively, there may be employed a guide member 99 as shown in FIG. 18, having at its distal end a convex holder portion 99a which is provided with a recess 99b to receive an end portion of the rotating member 97 of the connector section 95.

What is claimed is:

1. In endoscopically inserting ultrasound probe adapted to be placed in an instrument channel within an elongated insertion rod of an endoscope at the time of insertion into a body cavity, and having a probe head housing an ultrasound transducer at the fore distal end of an elongated flexible cord member with a connector section in a proximal end portion thereof for connection to a probe controller unit:

an endoscopically inserting ultrasound probe, comprising:

a probe head having an outside diameter larger than the inside diameter of an instrument channel within an endoscopic insertion rod; and an elongated flexible cord member having an outside diameter smaller than the inside diameter of endoscopic instrument channel, including a connector section provided at the proximal end of said flexible cord member;

said ultrasound probe being placed in the endoscopic instrument channel inversely through an exit opening of the instrument channel at the fore distal end of the endoscopic insertion rod and from said connector section at the proximal end of said flexible cord member.

2. An endoscopically inserting ultrasound probe as defined in claim 1, further comprising a probe head holder member fitted on a neck portion of said ultrasound probe head and disengageably engageable with said exit opening of said instrument channel for temporarily fixing said ultrasound probe head at said fore distal end of said endoscopic insertion rod.

3. An endoscopically inserting ultrasound probe as defined in claim 2, wherein said probe head holder member is formed of resilient material basically in the shape of an annular ring resiliently fixable in said exit opening of said instrument channel at the distal end of said endoscopic insertion rod and having an inside diameter smaller than the outside diameter of said neck portion of said ultrasound probe head.

4. An endoscopically inserting ultrasound probe as defined in claim 3, wherein said annular ring of resilient material is a split ring having an axial slot in a ring-like body thereof.

5. An endoscopically inserting ultrasound probe as defined in claim 3, wherein said annular ring of resilient material is provided with a flange portion around a fore end portion thereof, said flange portion serving as an anchor means for fixing one end of a balloon fitted on said ultrasound probe head.

6. An endoscopically inserting ultrasound probe as defined in claim 5, wherein said annular ring of resilient material is provided with a fluid passage axially through a cylindrical body thereof, said fluid passage having one end thereof opened into said endoscopic instrument channel and the other end into said balloon.

7. An endoscopically inserting ultrasound probe as defined in claim 2, wherein said probe head holder member is constituted by part of a hood member of resilient material adapted to be fitted on a fore distal end portion of said endoscopic insertion rod, said hood member having in a probe head holder portion an open cavity axially in alignment with said exit opening of said endoscopic instrument channel to receive and hold therein a neck portion of said ultrasound probe head and a fore end portion of said flexible cord member, said hood member having an open area side by side with said probe head holder portion to expose endoscopic observation means to the outside therethrough.

8. An endoscopically inserting ultrasound probe as defined in claim 7, wherein said hood member is provided with a hollow projection in communication with said cavity and on the side of said endoscopic insertion rod for engagement in said exit opening of said endoscopic instrument channel.

9. An endoscopically inserting ultrasound probe as defined in claim 7, wherein said hood member is provided with an extensional instrument channel in communication with said endoscopic instrument channel.

10. An endoscopically inserting ultrasound probe as defined in claim 1, further comprising a guide member having an elongated flexible body to be introduced into said endoscopic instruments channel through an entrance opening on a manipulating head assembly of said endoscope to meet said connector section of said cord member of said ultrasound probe at a point ahead of a branching point where said endoscopic instrument channel is divided into a passage leading to said entrance opening and a suction passage leading into said manipulating head assembly, said guide member being engageable with a proximal end portion of said connector section to guide the latter in the axial direction of said endoscopic instrument channel.

11. An endoscopically inserting ultrasound probe as defined in claim 10, wherein said guide member and said connector section of said ultrasound probe are arranged to be fitted one on the other.

12. An endoscopically inserting ultrasound probe as defined in claim 10, wherein said guide member is provided with a tubular socket portion to be fitted on an electrode member projected in said connector section of said ultrasound probe.

* * * * *